(12) United States Patent
Stierns

(10) Patent No.: US 11,415,255 B1
(45) Date of Patent: Aug. 16, 2022

(54) ASEPTIC FLUID COUPLINGS

(71) Applicant: Colder Products Company, Roseville, MN (US)

(72) Inventor: Thomas Michael Stierns, Zimmerman, MN (US)

(73) Assignee: Colder Products Company, Roseville, MN (US)

( * ) Notice: Subject to any disclaimer, the term of this patent is extended or adjusted under 35 U.S.C. 154(b) by 0 days.

(21) Appl. No.: 17/215,486

(22) Filed: Mar. 29, 2021

Related U.S. Application Data

(60) Provisional application No. 63/002,669, filed on Mar. 31, 2020.

(51) Int. Cl.
*B29C 65/18* (2006.01)
*F16L 37/38* (2006.01)
*F16L 37/244* (2006.01)

(52) U.S. Cl.
CPC .............. *F16L 37/38* (2013.01); *B29C 65/18* (2013.01); *F16L 37/244* (2013.01)

(58) Field of Classification Search
CPC ................................ F16L 37/38; B29C 65/18
USPC ...................................................... 156/308.2
See application file for complete search history.

(56) References Cited

U.S. PATENT DOCUMENTS

| | | | |
|---|---|---|---|
| 3,856,050 A | 12/1974 | Rooney | |
| 4,014,368 A | 3/1977 | Nelsen | |
| 4,628,965 A | 12/1986 | Passerell | |
| 6,679,529 B2 | 1/2004 | Johnson | |
| 6,814,726 B1 | 11/2004 | Lauer | |
| 6,874,522 B2 | 4/2005 | Anderson | |
| 8,800,603 B2 | 8/2014 | Zeyfang | |
| 9,726,308 B2 * | 8/2017 | Williams | .............. A61M 39/16 |
| 10,350,400 B2 | 7/2019 | Lee | |
| 10,449,350 B2 | 10/2019 | Gebauer | |

FOREIGN PATENT DOCUMENTS

EP          0633034         1/1995

\* cited by examiner

*Primary Examiner* — James D Sells
(74) *Attorney, Agent, or Firm* — Fish & Richardson P.C.

(57) ABSTRACT

This document describes aseptic fluid coupling devices for fluid systems and methods of manufacturing such aseptic fluid coupling devices. For example, this document describes aseptic fluid coupling devices that include removable membrane strips that protect the interior of the aseptic fluid coupling devices from contamination prior to use. Methods for attaching removable membranes to the aseptic fluid coupling devices are also described.

5 Claims, 4 Drawing Sheets

ASEPTIC FLUID COUPLINGS

CROSS-REFERENCE TO RELATED APPLICATIONS

This application claims the benefit of U.S. Provisional Application Ser. No. 63/002,669, filed Mar. 31, 2020. The disclosure of the prior application is considered part of (and is incorporated by reference in) the disclosure of this application.

BACKGROUND

1. Technical Field

This document relates to aseptic fluid coupling devices for fluid systems and methods of manufacturing such aseptic fluid coupling devices. For example, some embodiments described in this document relate to aseptic fluid coupling devices that include removable membrane strips that protect the interior of the aseptic fluid coupling devices from contamination prior to use.

2. Background Information

Some fluid systems, such as some bioprocessing fluid systems or blood handling systems, may require fluid couplings that can aseptically connect a fluid flow path. Aseptic coupling devices can be used to connect two or more sterilized pathways. For example, aseptic coupling devices can be used to couple a fluid pathway from a first piece of processing equipment or container to a fluid pathway from a second piece of processing equipment or container to establish a sterile pathway for fluid transfer therebetween.

SUMMARY

This document describes aseptic fluid coupling devices for fluid systems and methods of manufacturing such aseptic fluid coupling devices. For example, this document describes aseptic fluid coupling devices that include removable membrane strips that protect the interior of the aseptic fluid coupling devices from contamination prior to use.

In particular embodiments, the fluid coupling devices described herein are single-use devices because, after the two portions of the coupling (also referred to herein as "coupling halves" and/or "connectors") are connected to each other, the coupled portions are designed to resist uncoupling. For example, such single-use coupling devices are equipped with one or more mechanical components that operate like locks to maintain the two portions of the coupling in the coupled state. Hence, in these particular embodiments, the fluid coupling devices provided herein are structurally configured to be single-use connection devices so that, after the single-use coupling halves have been connected to each other, they cannot be operably disconnected from each other (as such, preserving the sterility or biological integrity of the system/flow path/etc.).

Additionally, in such single-use embodiments or in other embodiments, the fluid coupling devices can be configured as "aseptic" coupling devices in that can be connected to each other while inhibiting biological contamination from migrating into the flow paths. Such an "aseptic" coupling will also serve to limit the exposure of the fluid to the surrounding environment.

Further, in such single-use embodiments, or other embodiments, some of the fluid coupling devices described herein can be configured as genderless couplings. That is, the two coupling portions can be designed exactly alike so that there is no male or female coupling halves as in many conventional fluid coupling designs.

In one aspect, this disclosure is directed to aseptic couplings and methods for their use. In another aspect, this disclosure is directed to methods for manufacturing aseptic couplings.

For example, this disclosure is directed to a method of attaching a membrane to a surface of an aseptic fluid coupling device. The method includes (a) placing the membrane between the surface and a membrane bonding tool, wherein an annular seal member extends beyond the surface toward the membrane, and wherein the membrane bonding tool comprises: (i) a middle protruding portion and (ii) a heating ring surrounding the middle protruding portion, wherein a front face of the middle protruding portion extends beyond a heating surface of the heating ring; (b) placing the middle protruding portion in contact with the membrane and thereby deflecting the membrane into an interior of the annular seal member; and (c) after deflecting the membrane, compressing the membrane between the heating ring and the surface to create a bond between the membrane and the surface extending peripherally around the annular seal member.

Such a method may optionally include one or more of the following features. The heating ring may apply heat to the membrane to create the bond. The middle protruding portion may also deflect the annular seal member while deflecting the membrane. The membrane may cover the annular seal member and an opening to an interior of the aseptic fluid coupling device. The membrane may be removable from the surface so that the aseptic fluid coupling device can become functionally coupled with another aseptic fluid coupling device.

This disclosure is also directed to an aseptic fluid coupling device. The aseptic fluid coupling device includes: (a) a main body defining an interior passage and having a front face surface; (b) an annular seal member: (i) coupled to the main body, (ii) surrounding a portion of the interior passage, (iii) defining an inner diameter and an area within the inner diameter, and (iv) extending beyond the front face surface; and (c) a membrane removably bonded to the front face surface and covering the annular seal member. An area of the membrane covering the inner diameter of the seal member is larger than the area within the inner diameter of the seal member.

Such an aseptic coupling may optionally include one or more of the following features. The membrane may include a fold. The membrane may close an opening to the interior passage defined by the front face surface. The membrane may be bonded to the front face surface by a heat bonding. A free end of the membrane may include a handle portion.

Particular embodiments of the subject matter described in this document can be implemented to realize one or more of the following advantages. First, in some embodiments, the fluid coupling devices include removable membrane strips that prevent contamination of the fluid contacting surfaces of the couplings prior to use. Moreover, in some embodiments the removable membrane strips are attached to the fluid coupling devices in a manner by which tension stress of the membrane strips is minimized. Accordingly, the potential for premature, undesirable full or partial disconnections of the membrane strips from the fluid coupling is reduced.

Second, some embodiments of the fluid coupling devices provide an improved aseptic connection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the connection of particular fluid couplings in a sterile room or within a sterile flow-hood to prevent biological contamination.

Third, some embodiments of the fluid coupling devices provided herein are advantageously designed to be genderless. Accordingly, usage of the fluid coupling devices are simplified and a user may be able to carry less inventory of fluid coupling components. Also, the genderless aspect of the fluid couplings offers additional system flexibility because anything with one of these couplings can connect to anything else with another one of these couplings.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION OF ILLUSTRATIVE EMBODIMENTS

As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies.

As used herein, the term "aseptic" refers to any process that maintains a clean and sterilized surface or volume.

As used herein, the term "fluid" means any substance that can be made to flow including, but is not limited to, liquids, gases, granular or powdered solids, mixtures or emulsions of two or more fluids, suspensions of solids within liquids or gases, etc.

Figure 1:
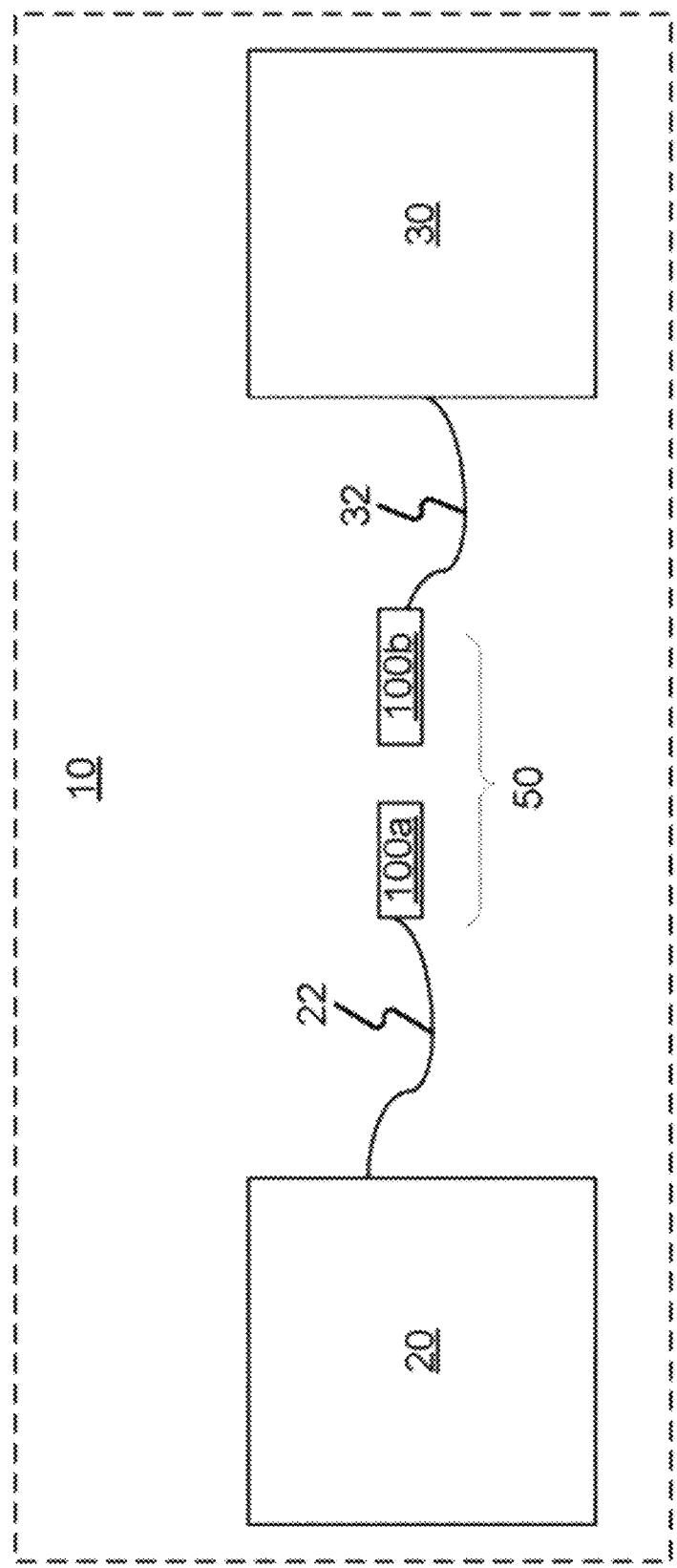
FIG. 1 is a schematic view of an example fluid system including an example fluid coupling arranged in a pre-connected configuration, in accordance with some embodiments provided herein.

Referring now to FIG. 1, an example system 10 is shown. System 10 includes a first piece of processing equipment 20 and a second piece of processing equipment 30. In example embodiments, equipment 20 and 30 are bioreactors including biomaterial. In other embodiments, equipment 20 and 30 can be other apparatuses that require a sterile connection therebetween such as, for example, a bioreactor and a media bag, sample bag, or other receptacle.

Equipment 20 includes a fluid pathway 22 extending therefrom that is terminated by an aseptic coupling arrangement 50 including a first aseptic coupling device 100a. Likewise, equipment 30 includes a fluid pathway 32 extending therefrom that is terminated by a second aseptic coupling device 100b of the aseptic coupling arrangement 50. The coupling arrangement 50 is representative of the multiple different aseptic couplings described herein.

In example embodiments, aseptic coupling devices 100a and 100b are substantially similar or genderless (e.g., identical except for possibly differences in terminations of the coupling devices 100a and 100b where other components, such as tubes, can be attached to the coupling devices 100a and 100b). However, it is noted that each aseptic coupling device 100a, 100b may be provided with different features than the other, as desired.

In example embodiments, the fluid containing environments within pathways 22 and 32 and aseptic coupling devices 100a and 100b are sterile. In some embodiments, the aseptic coupling arrangement 50 can be placed in an uncoupled configuration, one or more pre-coupled configurations, and in a coupled configuration, as described further below. In a pre-coupled configuration, while the coupling devices are mechanically coupled to each other, no fluid flow path is open therethrough.

The coupling devices 100a and 100b are designed and configured so that they can be reconfigured from the uncoupled state to the coupled state (e.g., to connect pathways 22 and 32) while preventing a loss of sterility of the fluid containing environments within the pathways 22 and 32. Hence, using the aseptic coupling arrangement 50, fluid can be transferred between equipment 20 and 30 (via coupling devices 100a and 100b) without becoming biocontaminated.

While the coupling devices 100a and 100b are uncoupled, and during the one or more pre-coupled configurations, each of the coupling devices 100a and 100b may include a removable membrane strip attached to a front face of the coupling devices 100a and 100b. Such a removable membrane strip serves to prevent the inside of the coupling device 100a/b from contamination until the coupling devices 100a and 100b are coupled together in a sterile manner.

Figure 2:
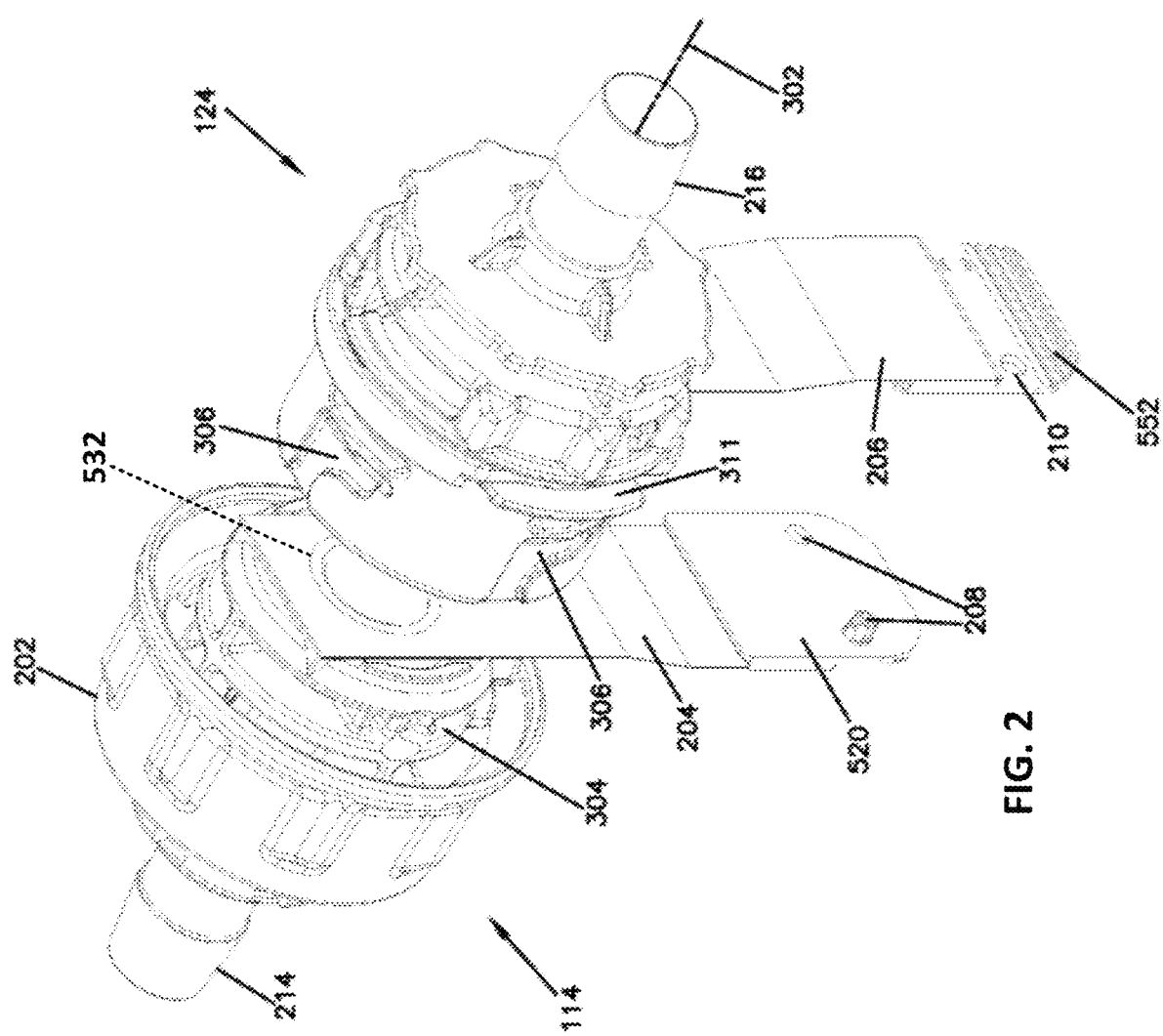
FIG. 2 is a perspective view of two example aseptic couplings prior to interconnection.

Referring also to FIG. 2, example aseptic coupling devices 114 and 124 are shown in an uncoupled state. In this state, the aseptic coupling devices 114, 124 are not yet connected to one another. In this state, contamination of the inside of the aseptic coupling device 114 is prevented by a removable membrane 204, and contamination of the inside of the aseptic coupling device 124 is prevented by a removable membrane 206 (that is, assuming that the termination portions 214 and 216 are coupled to sterile pathways 22 and 32 as depicted in FIG. 1).

In the example shown, aseptic coupling device 114 is a male coupling device, and aseptic coupling device 124 is a female coupling device. In the example shown, the devices 114, 124 are keyed so that the devices 114, 124 can only be coupled in one manner. In alternative embodiments, other configurations are possible. In some embodiments, the aseptic coupling devices 114, 124 make "clicking" noises as they are coupled together to provide the user with audible and/or tactile feedback of a positive coupling.

In the example shown, the male aseptic coupling device 114 includes an inner member 304, a locking ring 202, and the removable membrane 204.

Inner member 304 defines an interior fluid passage through aseptic coupling device 114. The removable membrane 204 prevents the interior fluid passage from becoming contaminated prior to the aseptic coupling devices 114 and 124 being coupled together. The inner member 304 includes, or is coupled to, a termination portion 214. In the example shown, the termination portion 214 is a barbed connection so that termination portion 214 can be connected to a fluid pathway such as a tube. Any type of termination can be used (e.g., sanitary fittings, compression fittings, threaded fittings, etc.). The locking ring 202 is rotatably coupled to the inner member 304.

The membrane 204 can be made of any suitable material including, but not limited to, polyethylene, polysulfone, polyester, PTFE, and the like. The membrane 204 can be a film, a foil (including metallic), and any other suitable thin flexible material and/or combinations of materials. In some embodiments, the membrane 204 is impervious to gases such as air. In some embodiments, the membrane 204 allows gaseous molecules to pass therethrough while blocking larger contaminant molecules. The membrane 204 is removably coupled using, for example, an adhesive to a front face surface of inner member 304 so as to cover an opening to the interior fluid passage through aseptic coupling device 114 that allows fluid flow through aseptic coupling device 114. In some embodiments, the membrane 204 is removably coupled by being welded (e.g., heat welding, ultrasonic welding, etc.) to a front face surface of inner member 304. Any suitable bonding technique to removably couple the membrane 204 to the front face surface of the inner member 304 can be used.

In the depicted embodiment, the male aseptic coupling device 114 includes a seal member 532 (not directly visible because it is covered in FIG. 2 by the removable membrane 204) positioned in a recess formed by the inner member 304. Seal member 532 is positioned to engage a corresponding seal member positioned in a recess of the aseptic coupling device 124 when aseptic coupling devices 114, 124 are connected and membranes 204, 206 are removed. The seal member 532 is an elastomeric annular ring with an open center through which the interior fluid passage of the male aseptic coupling device 114 passage extends (when the membrane 204 is removed).

A free end of the membrane 204 includes a handle portion 520 that includes attachment members 208 that are positioned to engage with attachment members 210 a handle portion 552 of the corresponding membrane 206 of the aseptic coupling device 124. With the aseptic coupling devices 114 and 124 coupled with each other and the handle portions 520 and 552 attached to each other, and a user can manually pull the handle portions 520 and 552 laterally away from the aseptic coupling devices 114 and 124 to remove the membranes 204 and 206 from the coupling devices 114 and 124 simultaneously. As the membranes 204 and 206 are removed, the seals (e.g., seal member 532) of the aseptic coupling devices 114 and 124 compress against each other to create an aseptic fluid passage through the coupling devices 114 and 124 along the longitudinal axis 302. The membranes 204 and 206 can be folded (e.g., at the top of the membranes 204 and 206 in the illustrative context of FIG. 2) so that the folds move in the direction of the pulling, and the membranes 204 and 206 thereby roll in on each other. In that manner, the membranes 204 and 206 can be stripped away without requiring excessive force, and no exterior potentially contaminated portions of membranes 204 and 206 will come in contact with the seal members. Accordingly, an aseptic connection between the aseptic coupling devices 114 and 124 can be created.

Figure 3:
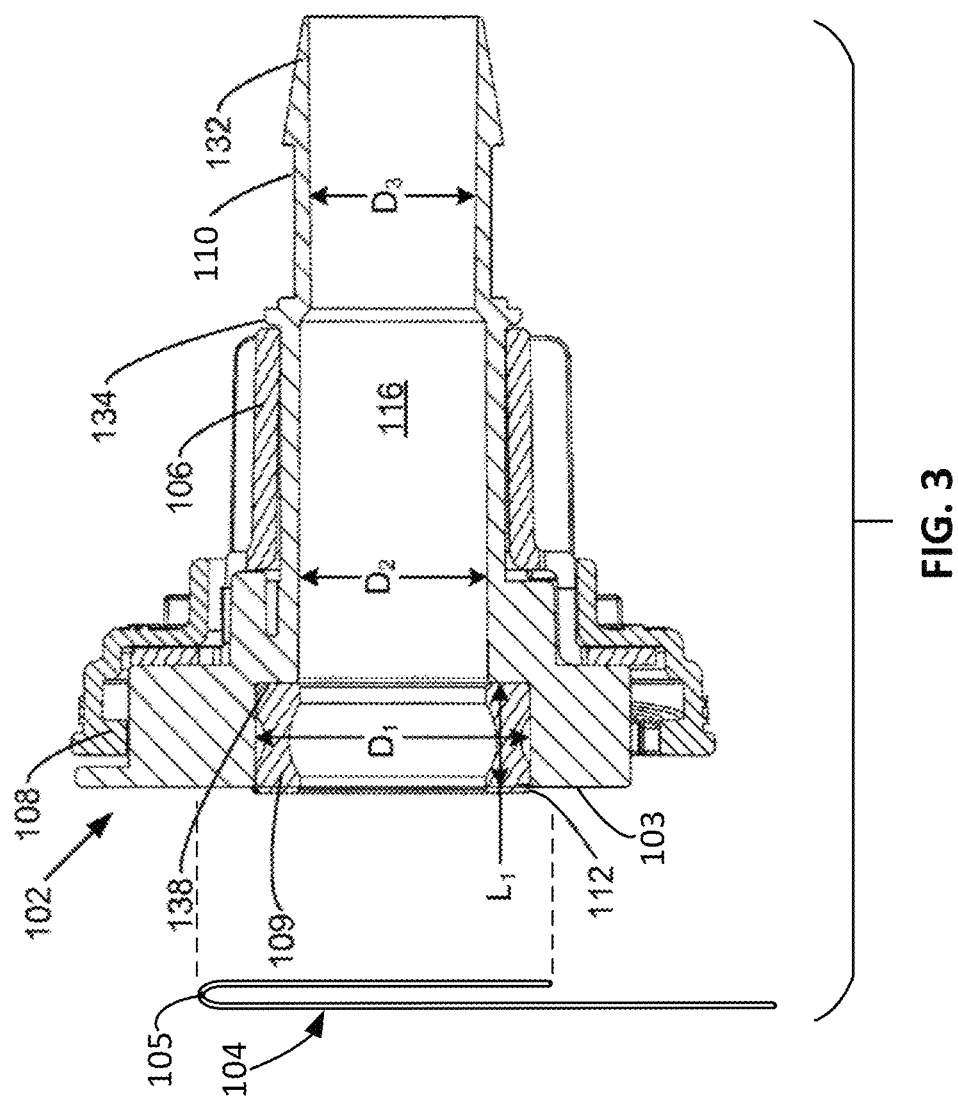
FIG. 3 is an exploded longitudinal cross-section view of another example aseptic coupling.

Referring to FIG. 3, another example aseptic coupling device 102 is depicted in an exploded longitudinal cross-section view. That is, the removable membrane 104 is shown separated from the main body 110 of the aseptic coupling device 102. In the normal uncoupled configuration of the aseptic coupling device 102, the removable membrane 104 is bonded to a front face 103 of the main body 110 so as to cover a seal member 109 and the interior 116 of the aseptic coupling device 102 from contamination. The fold 105 of the removable membrane 104 is clearly shown here.

The annular seal member 109 is positioned within a cylindrical recess 138 that is defined by the main body 110. The recess has a depth of Li. The width of the seal member 109 is slightly larger than the depth Li. Accordingly, an end portion 112 of the seal member 109 extends away or protrudes from the front face 103 of the main body 110 and toward the removable membrane 104. Put another way, the seal member 109 stands proud of the front face 103 of the main body 110.

Because the end portion 112 stands proud of the front face 103 of the main body 110, the end portion 112 tends to press against the removable membrane 104 while the removable membrane 104 is attached to the front face 103. Depending on the conditions under which the removable membrane 104 was bonded to the front face 103, the pressing of the end portion 112 against the removable membrane 104 may stress the bond to the point that it may at least partially detach. That may especially be the case while the aseptic coupling device 102 is subjected to high ambient temperatures such as during shipping and autoclaving (sterilization). In other words, when the ambient temperature is elevated, the bond strength between the removable membrane 104 and the front face 103 may be lessened to the extent that the pressing of the removable membrane 104 away from the front face 103 by the end portion 112 may overcome the bond strength between the removable membrane 104 and the front face 103. In such a condition, the bond between the removable membrane 104 and the front face 103 of the main body 110 may fail and the sterility of the interior of the aseptic coupling device 102 will be compromised.

For at least the foregoing reasons, it may be desirable to minimize the stress on the removable membrane 104 that is caused by the end portion 112 of the seal member 109. As described further below in reference to FIG. 4, the method by which the removable membrane 104 is bonded to the front face 103 of the main body 110 can serve to minimize the stress on the removable membrane 104 that is caused by the end portion 112 of the seal member 109.

Figure 4:
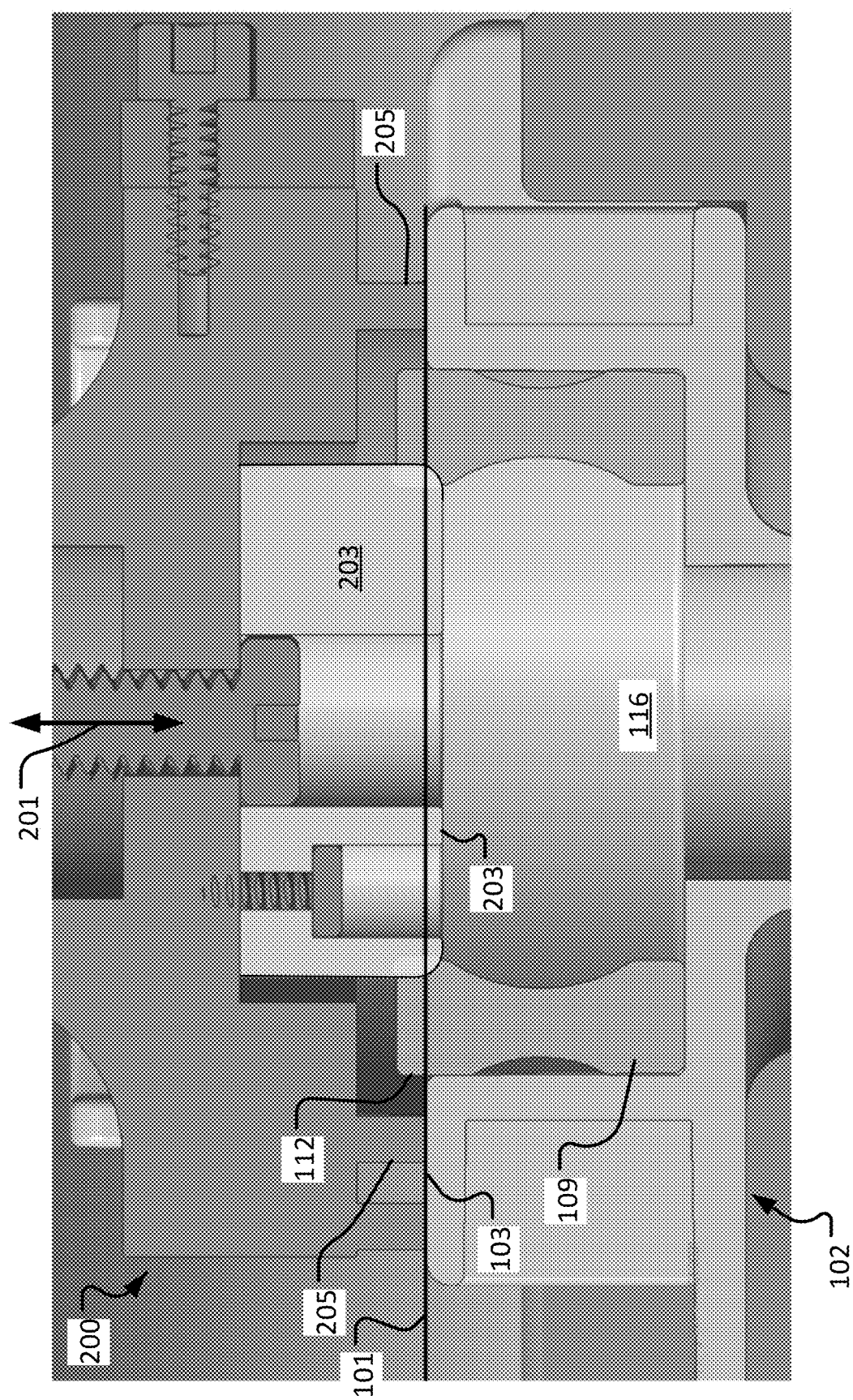
FIG. 4 is a longitudinal cross-section view of an example membrane bonding tool and an aseptic coupling that is being produced using the membrane bonding tool.

Referring also to FIG. 4, an example membrane bonding tool 200 can be used to bond the membrane 104 (not shown) to the front face 103 of the aseptic coupling device 102 during the manufacturing of the aseptic coupling device 102. Here, both the membrane bonding tool 200 and an end portion of the aseptic coupling device 102 are shown in a longitudinal cross-section view. The removable membrane 104 is not shown in FIG. 4.

The membrane bonding tool 200 is specifically designed to create a bond between the membrane 104 and the front face 103 of the aseptic coupling device 102 that is resistive to failure from the pressing of the removable membrane 104 away from the front face 103 by the end portion 112 (as described above).

During the manufacturing of the aseptic coupling device 102, the membrane bonding tool 200 can be moved toward and away from the front face 103 of the aseptic coupling device 102 as indicated by arrow 201. In particular, prior to the attachment of the membrane 104 to the front face 103 of the aseptic coupling device 102, the membrane bonding tool 200 is separated from the membrane 104 and the front face 103 of the aseptic coupling device 102. Then, with the membrane 104 held in the proper position relative to the front face 103, the membrane bonding tool 200 can be moved toward the membrane 104 and the front face 103 of the aseptic coupling device 102 such that contact therebetween is made (as shown in FIG. 4). This arrangement causes bonding of the membrane 104 to the front face 103 of the aseptic coupling device 102 because heat is applied by the membrane bonding tool 200 to cause the bonding of the membrane 104 to the front face 103 of the aseptic coupling device 102.

The membrane bonding tool 200 includes a cylindrical middle protruding portion 203 and a heating ring 205. It can be seen in FIG. 4 that the front face of the middle protruding portion 203 extends beyond the leading surface level of the heating surface of the heating ring 205 (where the plane of the leading surface of the heating ring 205 is indicated by the line 101). Accordingly, as the membrane bonding tool 200 is moved toward the membrane 104 and the front face 103 of the aseptic coupling device 102, the first contact therebetween is made by the face of the middle protruding portion 203 against the membrane 104. Such contact is made prior to contact between the heating ring 205 and the front face 103 of the aseptic coupling device 102.

Because the middle protruding portion 203 extends beyond the leading surface level of the heating ring 205 (line 101), as the membrane bonding tool 200 is moved toward the front face 103 the middle protruding portion 203 makes first contact against the membrane 104 and thereby pushes some amount of the membrane 104 into the interior of the sealing member 109. Accordingly, the area of the membrane 104 within the interior of the sealing member 109 is greater than the area within the interior of the sealing member 109. Then, while that portion of the membrane 104 is residing in the interior of the sealing member 109, the heating ring 205 subsequently contacts the membrane 104 and pushes it against the front face 103 of the aseptic coupling device 102 to create the bond between the membrane 104 and the front face 103 of the aseptic coupling device 102 (as depicted in FIG. 4).

In accordance with the preceding description, it can be understood that because the middle protruding portion 203 extends beyond the leading surface level of the heating ring 205, the middle protruding portion 203 causes some extra amount of the membrane 104 to be positioned within the periphery of the seal that is created between the membrane 104 and the front face 103 of the aseptic coupling device 102 when the seal is created (as compared to if no middle protruding portion 203 was used).

When, after creating the heat seal between the membrane 104 and the front face 103, the membrane bonding tool 200 is thereafter retracted away from the aseptic coupling device 102, the extra amount of the membrane 104 remains positioned within the periphery of the seal between the membrane 104 and the front face 103. This extra amount of the membrane 104 reduces or minimizes the tension of the membrane 104 positioned within the periphery of the seal between the membrane 104 and the front face 103.

Based on this description of the interactions between the membrane bonding tool 200 and the aseptic coupling device 102 during the heat-bonding process of the membrane 104 to the front face 103, it can be envisioned that an area of the membrane 104 covering the inner diameter of the sealing member 109 will be slightly larger than the area within the inner diameter of the sealing member 109. In some embodiments, the membrane 104 covering the inner diameter of the sealing member 109 will be at zero tension. In some embodiments, the membrane 104 will be at zero tension inside of the peripheral heat seal between the membrane 104 and the front face 103.

By varying the distance by which the middle protruding portion 203 extends beyond the leading surface level of the heating ring 205, the amount of tension of the membrane 104 within the periphery of the heat seal between the membrane 104 and the front face 103 can be selectively determined. That is, when the distance by which the middle protruding portion 203 extends beyond the leading surface level of the heating ring 205 is large, the resulting tension of the membrane 104 within the seal can be zero (e.g., the membrane 104 can be tensionless or even baggy within the seal). Conversely, when the distance by which the middle protruding portion 203 extends beyond the leading surface level of the heating ring 205 is made less, some small amount of tension of the membrane 104 within the seal can result. Accordingly, the resulting tension of the membrane 104 within the seal can be selectively reduced from the nominal amount (e.g., the amount resulting from bonding without pre-deflection of the membrane 104 as described herein) by any desired range of percentage (e.g., tension reductions of 80% to 100%, 70% to 90%, 60% to 80%, 50% to 70%, 40% to 60%, 30% to 50%, 20% to 40%, 10% to 30%, 0% to 20%, or 0% to 10%).

Selectively lessening the amount of tension of the membrane 104 within the periphery of the seal (using the membrane bonding tool 200 as described above) reduces the tendency of the seal between the membrane 104 and the front face 103 to subsequently become detached (e.g., during sterilization or transport, as described above). Accordingly, the manufacturing technique illustrated in FIG. 4 can serve to reduce the potential for failures of the seal between the removable membrane 104 and the front face 103 of the aseptic coupling device 102 (and of all types of aseptic coupling devices that use a removable membrane).

While the example membrane bonding tool 200 includes the middle protruding portion 203 that contacts the membrane 104 from the outside of the aseptic coupling device 102, alternatively a protruding portion can make contact with the membrane 104 from the interior 116 of the aseptic coupling device 102. In such a case, the interior protruding member can create a slight tent of the membrane 104 and then the heating ring 205 can be applied to bond the membrane 104 to the front face 103 of the aseptic coupling device 102.

While the above techniques describe deflecting a middle portion of the membrane 104 and then (while maintaining the deflection) bonding the membrane 104 to the aseptic coupling device 102, in some embodiments the membrane 104 is pre-formed in a separate prior process and then the pre-formed membrane 104 is subsequently bonded to the aseptic coupling device 102. The end result of the aseptic coupling device 102 with the pre-formed membrane 104 bonded thereto can be the same as described herein (e.g., zero or some small amount of tension of the membrane 104 within the seal can result).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of attaching a membrane to a surface of an aseptic fluid coupling device, the method comprising:
    placing the membrane between the surface and a membrane bonding tool, wherein an annular seal member extends beyond the surface toward the membrane, and wherein the membrane bonding tool comprises: (i) a middle protruding portion and (ii) a heating ring surrounding the middle protruding portion, wherein a front face of the middle protruding portion extends beyond a heating surface of the heating ring;
    placing the middle protruding portion in contact with the membrane and thereby deflecting the membrane into an interior of the annular seal member; and
    after deflecting the membrane, compressing the membrane between the heating ring and the surface to create a bond between the membrane and the surface extending peripherally around the annular seal member.

2. The method of claim 1, wherein the heating ring applies heat to the membrane to create the bond.

3. The method of claim 1, wherein the middle protruding portion also deflects the annular seal member while deflecting the membrane.

4. The method of claim 1, wherein, when the membrane is attached to the surface, the membrane covers the annular seal member and an opening to an interior of the aseptic fluid coupling device.

5. The method of claim 4, wherein the membrane is removable from the surface so that the aseptic fluid coupling device can become functionally coupled with another aseptic fluid coupling device.

* * * * *